United States Patent [19]
Gogolewski et al.

[11] Patent Number: 5,527,341
[45] Date of Patent: Jun. 18, 1996

[54] RESORBABLE TENDON AND BONE AUGMENTATION DEVICE

[75] Inventors: Sylwester Gogolewski, Alvaneu-Dorf; Martin Beck, Lucerne; Christian Gerber, Berne; Alberto G. Schneeberger, Davos; Stephan M. Perren, Davos-Dorf, all of Switzerland

[73] Assignee: Synthes (U.S.A), Paoli, Pa.

[21] Appl. No.: 297,975

[22] Filed: Aug. 30, 1994

Related U.S. Application Data

[63] Continuation of Ser. No. 17,331, Feb. 11, 1993, abandoned, which is a continuation of Ser. No. 705,389, May 24, 1991, abandoned.

[51] Int. Cl.⁶ .................................................. A61B 17/00
[52] U.S. Cl. ........................... 606/232; 606/233; 606/148
[58] Field of Search ........................ 606/232, 233, 606/60, 148–151, 228, 230, 69, 77; 623/11, 16

[56] References Cited

U.S. PATENT DOCUMENTS

| | | | |
|---|---|---|---|
| 2,199,025 | 4/1940 | Conn | 606/233 |
| 3,739,773 | 6/1973 | Schmitt | 604/891 |
| 3,931,821 | 1/1976 | Kletschka | 606/233 |
| 3,976,079 | 8/1976 | Samuels | 606/232 |
| 4,210,148 | 7/1980 | Stivala | 606/232 |
| 4,512,038 | 4/1985 | Alexander et al. | 606/69 X |
| 4,609,551 | 9/1986 | Caplan | 623/16 |
| 4,789,732 | 12/1988 | Urist | 623/16 |
| 4,823,794 | 4/1989 | Pierce | 606/232 |
| 4,882,149 | 11/1989 | Spector | 623/16 |
| 4,905,680 | 3/1990 | Tunc | 606/69 |
| 4,968,317 | 11/1990 | Törmälä | 606/77 |
| 4,990,161 | 2/1991 | Kampner | 623/16 |
| 5,013,292 | 5/1991 | Lemay | 606/232 |
| 5,219,359 | 6/1993 | McQuilkin | 606/232 |
| 5,366,480 | 11/1994 | Corrireau | 606/232 |

FOREIGN PATENT DOCUMENTS

| | | | |
|---|---|---|---|
| 3144125 | 5/1989 | European Pat. Off. | 606/151 |
| 2422386 | 11/1979 | France . | |
| 2947985 | 9/1981 | Germany . | |
| 9002844 | 12/1990 | Germany . | |
| 61-14067 | 4/1994 | Japan | 606/232 |
| 2114894 | 9/1983 | United Kingdom | 606/148 |
| 8803417 | 5/1988 | WIPO . | |
| 8806872 | 9/1988 | WIPO . | |

OTHER PUBLICATIONS

Parsons et al., Development of a Variable Stiffness Absorbable Bone Plate, 25th Annual ORS, 1979.

*Primary Examiner*—Robert A. Hafer
*Assistant Examiner*—David J. Kenealy
*Attorney, Agent, or Firm*—McAulay Fisher Nissen Goldberg & Kiel

[57] ABSTRACT

The device is implantable in the living body for attachment and augmentation of tendons and/or reinforcement of bones. It comprises a substantially flat membrane having a rounded outer shape and at least two perforations. The membrane contains resorbable or degradable polymeric and/or polymeric-ceramic material, having a Young's modulus in the range of 1 to 50 GPa and a tensile strength in the range of 0.1 to 20.0 GPa. It allows a more secure fixation of transosseous sutures.

2 Claims, 6 Drawing Sheets

RESORBABLE TENDON AND BONE AUGMENTATION DEVICE

This is a continuation of application Ser. No. 08/017,331, filed Feb. 11, 1993, which is a continuation of Ser. No. 07/705,389, filed May 24, 1991, both abandoned.

BACKGROUND OF THE INVENTION

1. Field of the invention

This invention relates to a device implantable in the living body for attachment and augmentation of tendons and/or reinforcements of bones.

The device according to the invention is particularly useful for the attachment and augmentation of the disrupted tendons of the rotator cuffs and the reinforcement of the proximal humeral bone.

Disorders of the rotator cuff are the most common cause of painful shoulder disability. The natural history of untreated ruptures of the rotator cuff are much less favourable than previously thought. Attempts of surgical repair of ruptures almost consistently yield satisfactory pain relief, in contrast to functional restoration which is less certain, particularly in large tears. This has been attributed to a variety of factors:

- the quality of muscle motoring the tendon may be irrevocably poor;
- the quality of the tendon (circulation, elasticity, tensile strength) may preclude repair;
- the quality of cancellous bone may not provide enough stability (e.g. in the case of osteoporosis); or
- the patient's lack of cooperation may defeat the surgical goal.

It has been established, that functional restoration of the shoulder does not depend on the cuff rotator tear size, but on the success of repair of the defect. Thus the anatomical and mechanical success of operative tendon-to-bone attachment is therefore of great importance.

Several factors, which influence the quality of repair such as the suture material, the quality of initial fixation, the tension in the musculotendinous unit and the load applied during the postoperative course influence the success of the repair. One of the important problems is how to grasp the tendon with the suture material to achieve a strong and secure attachment of the tendon to the bone.

2. Description of the Prior Art

Very few literature data concerning this problem are available and yet refer to the surgical attachment of the supraspinatus tendon, e.g. as described in an article of France, Paulos, Harner and Straight "Biomechanical evaluation of rotator cuff fixation methods" published in Am J Sports Med 17:176–181,1989.

Different prior art methods of soft tissue-to-bone fixation have been evaluated, e.g. fixation to bone by spiked washers and screws, using spiked soft tissue plates, different kinds of staples and suturing. It has been found that independently on the suturing technique used, the suture material pulls through the tendon.

It has been also observed that when using prior art non-augmented techniques for the tendon-to-bone attachment [e.g. according to the Kessler technique described in ML Mason, HS Allen, "The rate of healing of tendons An . experimental study of tensile strength", Ann Surg 113-3, 424–59(1941);

AD Forward, J Cowan, "Tendon suture to bone", J Bone Joint Surg 45-A(4), 807–823(1963); and LD Ketchum, NL Martin, DA Kappel, "Experimental evaluation of factors affecting the strength of tendon repairs", Plast Reconstr Surg 59(5), 708–719(1977)] there is a diastasis formed between connected elements, while suture applied to the tendon strangulates and/or pulls out the tendinous tissue.

Attempts have been made (France, Paulos, Harner and Straight "Biomechanical evaluation of rotator cuff fixation methods" published in Am J Sports Med 17:176–181,1989) to strengthen tendon-suture interface by interposing a polytetrafluoroethylene (PTFE) membrane between suture and tendon. Although it was expected that the membrane will augment the holding power of the tendon, no significant improvement was observed.

In addition it was observed in reoperations that shoulder function is usually not achieved, because of diastasis between the tendon and bone. While the suture material stays always intact, the tendon is connected to the bone through functionally insufficient scar tissue.

SUMMARY OF THE INVENTION

The invention as claimed is intended to remedy these drawbacks. It solves the problem of how to design a device implantable in the living body for attachment and augmentation of tendons and reinforcement of bones having a superior tensile strength of the tendon repair and/or allowing a more secure fixation of transosseous sutures.

The invention solves the problem with a device comprising a substantially flat membrane having a rounded outer shape and at least two perforations; the membrane material having a Young's modulus in the range of 1 to 50 GPa and a tensile strength n the range of 0.1 to 20.0 GPa.

The device according to the invention comprises a substantially flat membrane having a rounded outer shape and at least two perforations.

The membrane contains resorbable or degradable polymeric and/or polymeric-ceramic material having a Young's modulus in the range of 1 to 50 GPa and a tensile strength in the range of 0.1 to 20.0 GPa and preferably of non-porous structure.

Young's modulus is preferably in the range of 5 to 15 GPa and most preferably in the range of 7 to 10 GPa. Tensile strength is in the range of 0.5 to 3.0 GPa and most preferably in the range of 0.7 to 2.5 GPa.

Resorbable materials to be used for the device according to the invention can be resorbable polymers like highly purified polyhydroxyacids, polysaccharides, polyamines, polyaminoacids, polyorthoesters, polyanhydrides, polyamidoesters, polydixanone, polyesteramides, copolyoxalates, polycarbonates or poly(glutamic-co-leucine). Preferably polylactides are used or their combinations with polyhydroxybutyrates or polyhydroxyvalerates and/or resorbable glasses. Other useful polyhydroxyacids comprise polycaprolactone, poly(L-lactide), poly(DL-lactide), polyglycolide, poly(DL-lactide-co-glycolide), poly(DL-lactide-co-caprolactone).

Purposefully at least 90 weight percent of the resorbable polymeric material should have a molecular weight in the range of 200,000 to 400,000, preferably in range of 300,000 to 350,000.

In terms of molecular weight distribution, (or polydispersity) the polymeric and/or polymeric-ceramic material should have a polydispersity in the range of 1.2 to 100.0, preferably in the range of 1.5 to 3.0.

The resorbability of said material should be set at a level allowing to maintain adequate mechanical properties in vivo for at least 6 months, and preferably 7 months. The resorption rate can be adjusted to a desired value by altering the polymer molecular weight, the polymer chain orientation and crystallinity, physical structure, chemical composition, presence and extent of voids, additives a.s.o. By way of example poly(L-dL lactide) with 5% of dL-units and a molecular weight of 400.000 Daltons resorbs at the rate which assures augmentation during the healing time. Another example for a suitably resorbable material which maintains the required mechanical properties till the healing is complete is poly(L-lactide) with a molecular weight of 320.000 Daltons hot drawn to draw ratio 4. Still another example is poly(L-lactide) with a porosity in the range of 0.1 to 0.5 μm and a molecular weight of 300.000 Daltons which maintains 70% of its initial tensile strength 6 months after implantation.

Additionally to these resorbable materials according to the invention, other nonresorbable materials such as bioceramics (e.g. aluminium oxide ceramics), titanium, titanium alloys alone or coated with ceramics may be used to temporarily strengthen the device according to the invention. These nonresorbable materials, however, have to be removed from the implantation site after the healing is completed.

The resorbable materials to be used with the invention must be of non-porous structure to avoid tissue ingrowth, which would interfere with the gliding function of the tendon.

The resorbable polymeric tendon and/or bone augmentation device according to the invention can be produced either from a thin nonporous film, membrane or plate or likewise from a film, membrane or plate with controlled porosity and in vivo resorption time.

The thickness of the membrane can be controlled to meet structural demands of the proposed implantation site, but should range between 0.5 and 6.0 mm, preferably between 1.0 and 2.0 mm and most preferably between 1.4 and 1.5 mm.

The augmentation device according to the invention can also be used as a drug delivery device, containing antibiotics and/or fibroblast growth factor.

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

BRIEF DESCRIPTION OF THE DRAWINGS

FIG. 2b is a section through the device according to FIG. 2a;

DESCRIPTION OF THE PREFERRED EMBODIMENTS

Figure 1:
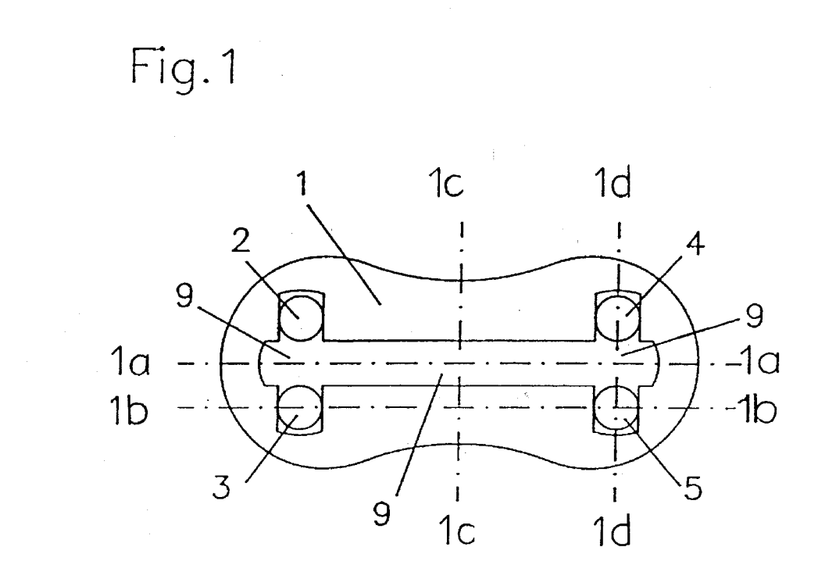
FIG. 1 is an elevational view of a tendon augmentation device according to the invention having a longitudinal shape with sectional views at locations 1A—1A, 1B—1B, 1C—1C and 1D—1D.
Figures 1A, 1B:
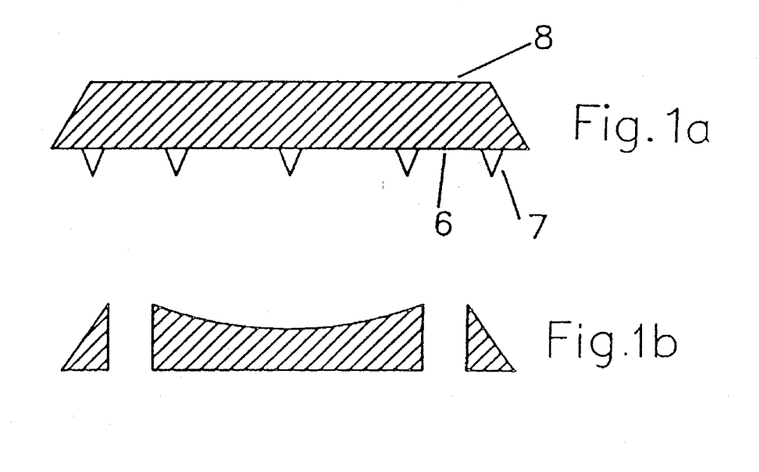
Figures 1C, 1D:
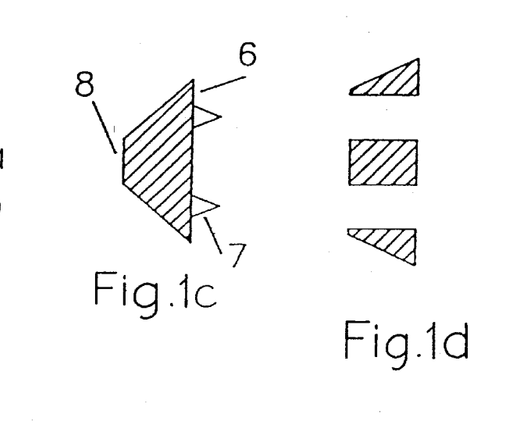

FIG. 1 shows a device according to the invention consisting of a substantially flat membrane 1 having a rounded outer shape, with the approximate dimensions of 5.0×10.0× 1.4 mm, having two pairs of lateral holes 2,3 and 4,5 with diameters in the range of 0.2 to 2.5 mm, and preferably 1 mm, to house the suture. All edges of the device are rounded to prevent irritation of the tissue and diminish the chance of suture damage due to friction. The surface 6 of the device which faces the tendon has 0.5 mm long spikes 7 to prevent slippage of the device on the tendon. The opposite surface 8 of the flat membrane 1 of the device is strengthened by incorporation of three bars 9 of the same material as the membrane 1.

Figure 2A:
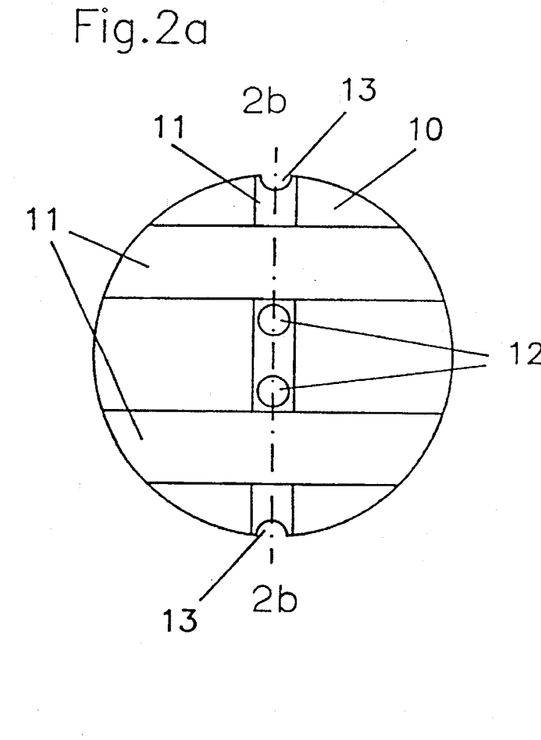
FIG. 2a is an elevational view of a device according to the invention having a circular shape.
Figure 2B:
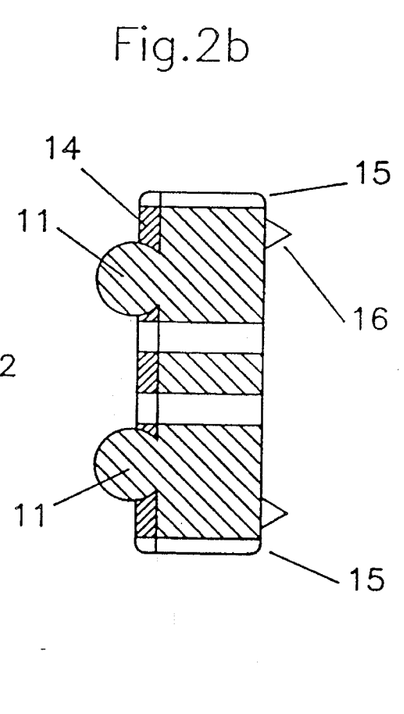
Figure 2C:
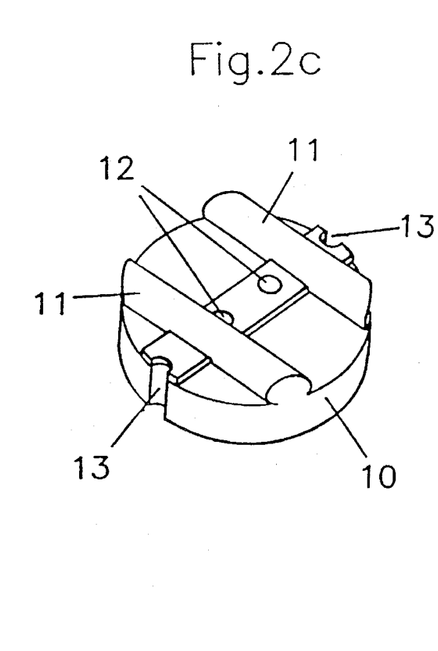
FIG. 2c is a perspective view of the device according to FIGS. 2a and 2b.

FIGS. 2a, 2b and 2c show a tendon augmentation device according to the invention which has a circular shape in the form of a disk 10. The diameter of the disk 10 is about 8 mm and its thickness about 2 mm. The disk 10 has two or three 0.5 mm thick reinforcing bars 11 of the same material as the disk to support the suture and two holes 12 with a diameter of 0.5 to 1.3 mm to house the suture and two cuts 13 at the edges of disk 10 to protect against slippage of the suture over the device. The surface 14 of the device facing the tendon has rounded edges 15 to diminish irritation and 0.5 to 1.0 mm long spikes 16 to prevent slippage of the device on the tendon.

Figure 3:
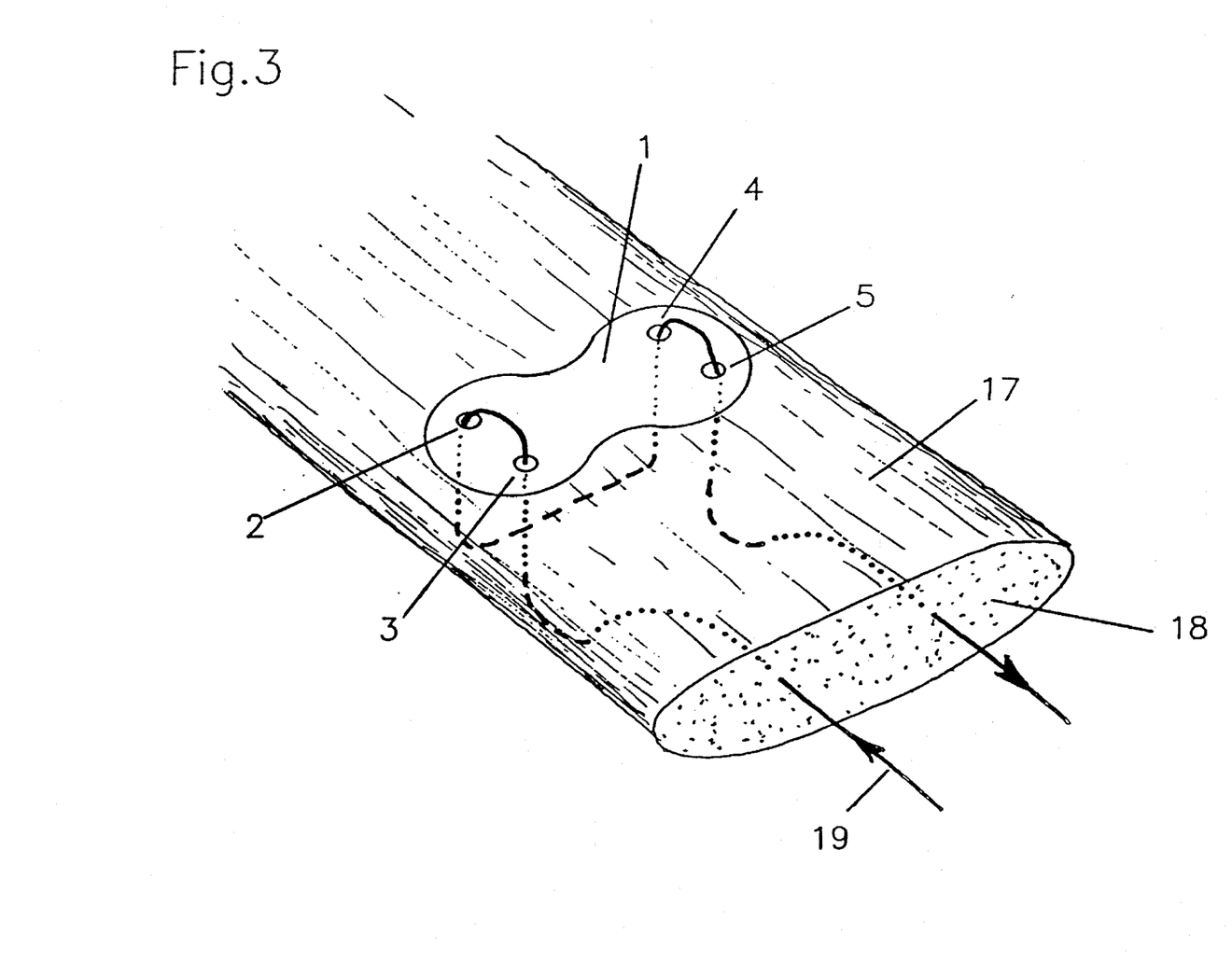
FIG. 3 is a perspective view of the tendon augmentation device according to FIG. 1 applied on a tendon.

As illustrated in FIG. 3 the tendon augmentation device 1 according to FIG. 1 is used for repairing and augmenting a disrupted tendon in a living body. The surgical method comprises the following steps:

A. Placing the augmentation device 1 intraoperatively on the surface 17 of the tendon 18.

B. Pulling proximally, along the tendon direction, the suture 19 from the cut end of tendon 18, towards its outer surface.

C. Pulling the suture 19 through the tendon 18 and one pair of two lateral holes 3,2 and towards the outer surface of the tendon 18.

D. Pulling the suture 19 back through the tendon 18 and the other pair of lateral holes 4,5 towards its outer surface.

E. Pulling the suture 19 longitudinally through the tendon 18 to its distal cut end.

Once fixed to the tendon the membrane 1 prevents the suture 19 from cutting through the tendon 18 at the point of highest stress (pulley).

Figure 4:
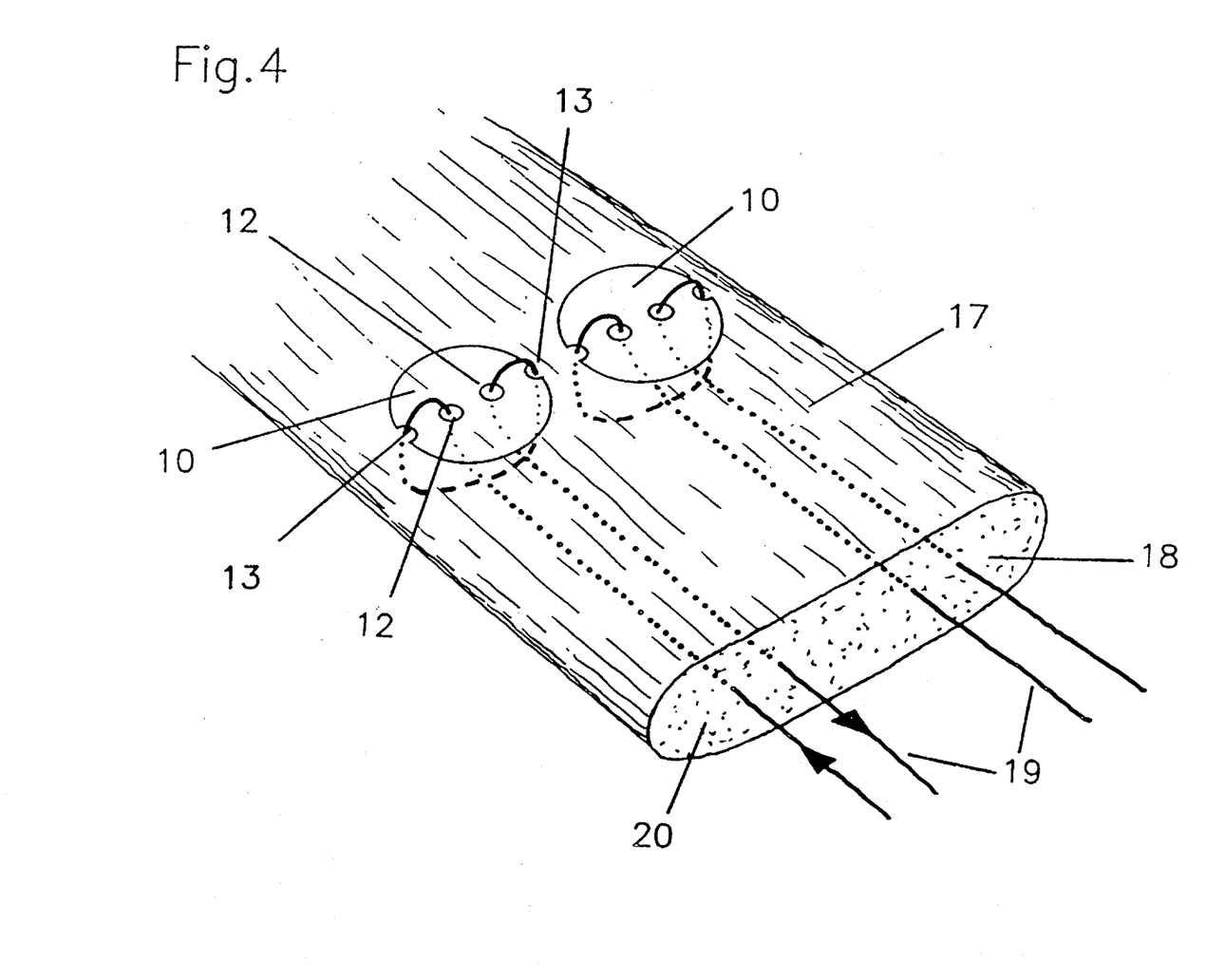
FIG. 4 is a perspective view of a pair of tendon augmentation devices according to FIG. 2 applied on a tendon.

The same operative technique is illustrated in FIG. 4 when a pair of disk-shaped devices 10 according to FIG. 2 are used. The operative method comprises:

A. Placing a first device 10 according to claim 5 on the surface 17 of the tendon 18.

B. Pulling proximally, along the tendon direction, a suture 19 from the cut end 20 of tendon 18 towards the device 10 and through one of its holes 12 to its outer surface.

C. Pulling the suture 19 through one of the cuts 13 into the tendon 18 towards to outer surface of the tendon 18.

D. Pulling the suture 19 back into the tendon 18 through the other cut 13 and the other hole 12 and again into the tendon 18.

E. Pulling the suture 19 longitudinally through the tendon 18 to its distal cut end.

F. Placing a second device 10 according to claim 5 on the surface 17 of the tendon 18 and performing steps B to E.

In vitro tests showed that the use of resorbable tendon augmentation devices according to the invention for the augmentation of the supraspinatus tendon, increased the pull out strength up to 469N (126%), as compared with the nonaugmented suture technique (with a tensile strength of 371N only).

Figure 5:
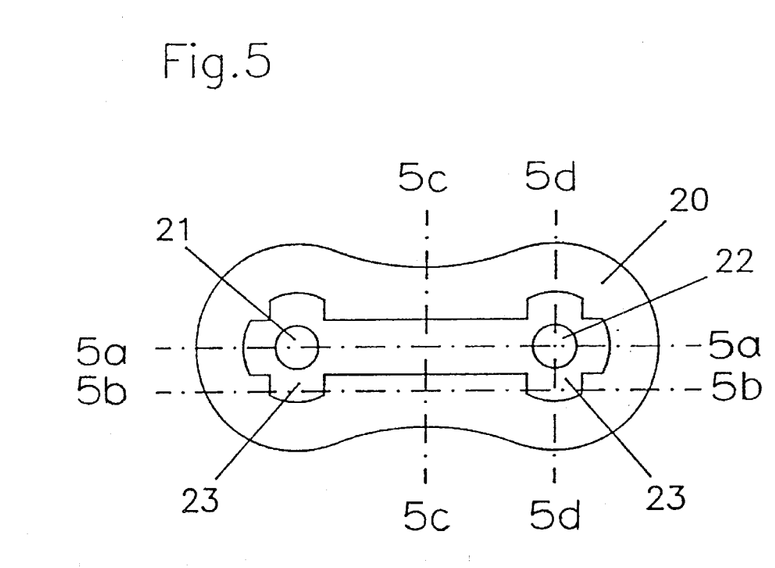
FIG. 5 is an elevational view of a bone augmentation device according to the invention having a longitudinal shape with sectional views at locations 1A—1A, 1B—1B, 1C—1C and 1D—1D.
Figure 5A:
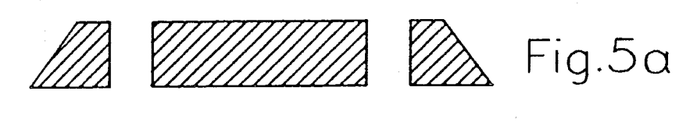
Figure 5B:
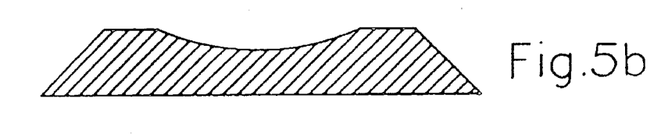
Figure 5C:
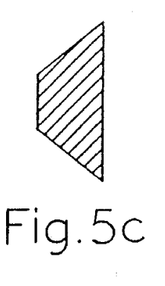
Figure 5D:
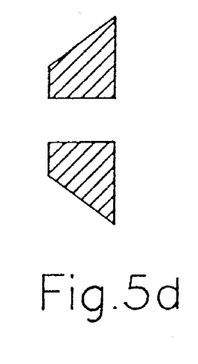

FIG. 5 shows a bone augmentation device consisting of a membrane 20 similar to the one used for the tendon augmentation device according to FIG. 1. It is fashioned into a rectangle, preferably with dimensions of 5.0×10.0×1.4 mm, with rounded edges to prevent irritation of the surrounding tissue and diminish friction between the suture and the device. The membrane 20 has two holes 21,22 and three reinforcing bars 23. Intraoperatively the device according to FIG. 5 is placed onto the osteoporotic bone of e.g. the humeral head. The suture is pulled through the holes 21,22 while the device acts as a washer. In vivo tests in the sheep with the resorbable device according to FIG. 5 to augment the bone showed to increase its holding power to 398N (520%), as compared with 76N for the nonaugmented cancellous bone. It allows therefore a more secure fixation of transosseous sutures to the bone.

Figure 6:
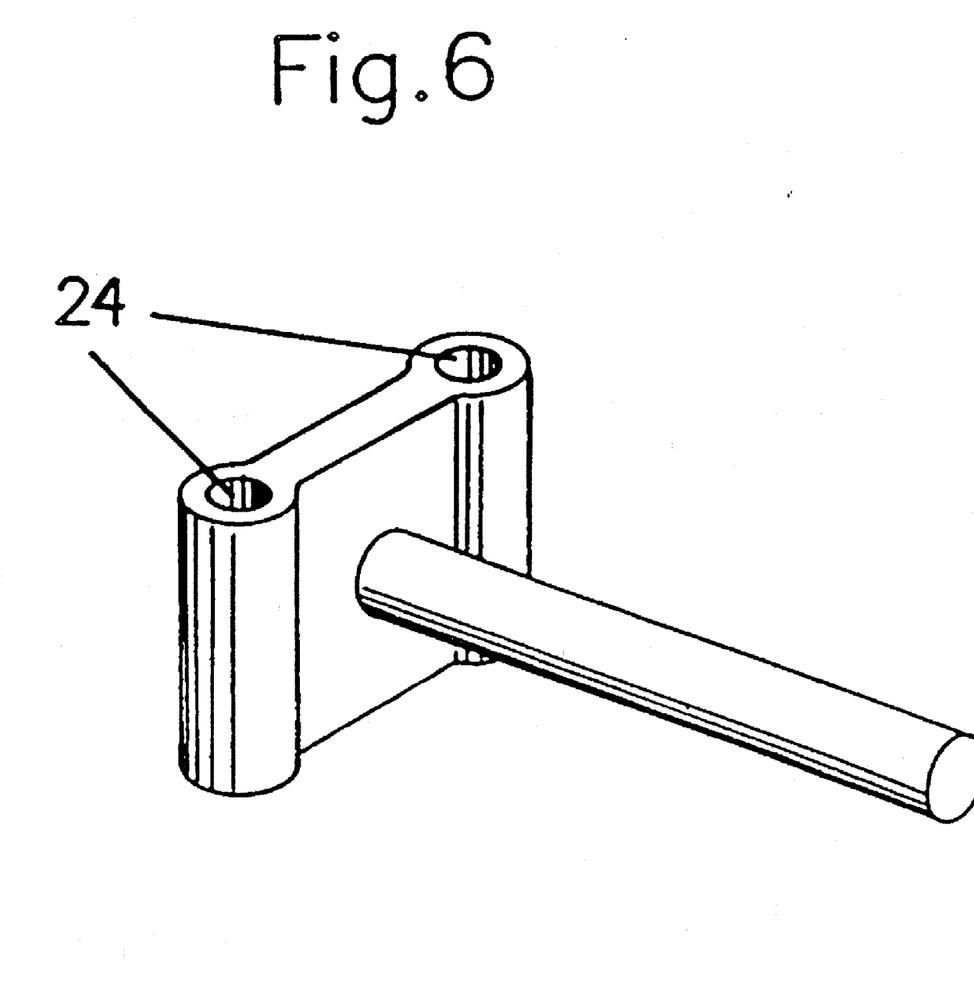
FIG. 6 is a perspective view of a drillin jig for effecting of the necessary bone perforations.

A similar surgical technique is used for the bone augmentation device but care should be taken that the holes drilled into the bone have identical distances between them as in the device to be secured to it in order to prevent cutting the bone by the suture material and diastasis which can be formed when the bone is cut. to achieve a high accuracy which is desirable it is recommended to use a special drill guide 22 as shown in FIG. 6 with guiding holes 21 corresponding exactly to the holes 12 of the device 10 to be secured to the bone.

The use of both, the tendon and the bone augmentation devices according to the invention have several advantages as compared with existing repair techniques. Thus, it reduces diastasis between the tendon and the bone being the main problem in the rotator cuff tear repair, it protects against tendon strangulation and cutting through the tendon and the osteoporotic bone at the place of fixation. The use of resorbable augmentation devices according to the invention has also additional advantages, i.e. once the device is resorbed, it no longer affects the already critical blood supply.

The tendon and bone augmentation device according to the invention can be prepared using one of the common techniques applied to polymer processing, e.g. injection-moulding, extrusion, compression-molding, solution-casting, etc. The devices can be produced as a composite device consisting of a resorbable polymer reinforced with resorbable polymeric and/or glass fibres.

Examples for manufacture:

I. A nonporous membrane with dimensions of 5.0×10.0×1.4 mm was prepared by casting from 10 wt.-% solution of poly(L-lactide) in chloroform at room temperature. Poly(L-lactide) with viscosity-average molecular weight of 350.000 Daltons used for preparation of the membrane was purified twice by dissolution in chloroform followed by precipitation with a methanol/water mixture. Membranes were dried to constant weight in vacuum oven at 70°. Augmentation devices of the required size were cut out from the membranes using a steel stamp. When used to augment the supraspinatus tendon they increased the pull out strength of the tendon to 470 N as compared with 370N for nonaugmented tendons.

II. A nonporous membrane with dimensions of 5.0×10.0×0.7 mm was prepared by casting from 7 weight-percent solution of poly(L-lactide) with a viscosity-average molecular weight of 350.000 Daltons in chloroform. When used to augment osteoporotic bone it increased the holding strength of the bone from 70N to 270N.

III. A nonporous membrane with dimensions of 5.0×10.0×1.4 mm was prepared by injection molding of highly purified poly(L-lactide) with a viscosity-average molecular weight of 340.000 Daltons. The polymer was dried and kept under vacuum prior to injection-moulding to diminish thermomechanical degradation. The augmentation device placed on osteoporotic bone of the humeral head increased the holding strength of the bone from 75N to 400N.

IV. A porous membrane with porosity in the range in the range of 0.5 to 1.0 μm and dimensions of 5.0×10.0×2.0 mm was prepared by solution casting from poly(L-lactide) with molecular weight of 240.000 Daltons. The augmentation device was cut out from the membrane using a steel stamp with a suitable shape. Reinforcing bars pressed in the microporous device using a suitable mould/hydraulic press system. The augmentation device placed on osteoporotic bone of the humeral head increased the holding strength of the bone from 80 to 310N.

V. Several manufacturing processes can be used to include reinforcing bars into the augmentation devices:

a) Injection molding:

The mould used for preparation of the augmentation device has a shape which allows formation of the reinforcing bars in one injection-molding operation;

b) Extrusion:

The polymer ribbon is extruded through a nozzle having a shape of a device with the reinforcing bars. The final device is cut out from the ribbon using a suitable stamp.

c) Solution casting:

A membrane is prepared by solution casting. Next the membrane is placed in a mould with a suitable shape and subsequently compression moulded at temperatures in the range of 80° to 110° C.

I claim:

1. A method of connecting a first and second tissue in a living body, the first tissue having an outer surface and a distal cut end, the method comprising the steps of:

(1) placing a substantially flat membrane having a rounded outer shape, a tendon/bone facing surface, and two pairs of perforations; the membrane containing resorbable or degradable polymeric material having a Young's modulus in the range of 1 to 50 GPa and a tensile strength in the range of 0.1 to 20.0 GPa on the outer surface of the first tissue with the tendon/bone facing surface contacting the outer surface of the first tissue, the membrane being placed wholly on the first tissue;

(2) pulling a suture, which enters the first tissue through the distal cut end, through the first tissue in a longitudinal direction;

(3) pulling the suture through the outer surface of the first tissue at an area opposite that where the flat membrane is placed;

(4) inserting the suture into the first tissue below a perforation in the flat membrane and pulling the suture through the first tissue and the perforation in the membrane;

(5) inserting the suture into the paired perforation in the membrane and pulling the suture through paired perforation in the membrane and the first tissue;

(6) repeating steps (4) and (5) for remaining paired perforations;

(7) inserting the suture into the first tissue and pulling the suture through the first tissue in the longitudinal direction toward the distal cut end;

(8) attaching the ends of the suture to the second tissue.

2. A method of connecting a first and second tissue in a living body, the first tissue having an outer surface and a distal cut end, the method comprising the steps of:

(1) placing a first substantially flat membrane having a circular outer shape, a tendon/bone facing surface, two perforations and two corresponding cuts; the membrane containing resorbable or degradable polymeric material having a Young's modulus in the range of 1 to 50 GPa and a tensile strength in the range of 0.1 to 20.0 GPa on the outer surface of the first tissue with the tendon/bone facing surface contacting the first tissue, the membrane being placed wholly on the first tissue;

(2) inserting a suture into the distal cut end of the first tissue and pulling the suture longitudinally through the first tissue toward the first circular membrane;

(3) pulling the suture through the outer surface and one of the perforations in the circular membrane;

(4) inserting the suture into the outer surface proximate to the membrane cut corresponding to the membrane perforation and pulling the suture through the first tissue causing the suture to pierce the outer surface of the first tissue, opposite the circular membrane.

(5) pulling the suture into the first tissue below the remaining cut and causing the suture to exit the first tissue proximate to the remaining cut in the membrane;

(6) inserting the suture into the remaining perforation in the membrane and pulling the suture back into the first tissue;

(7) pulling the suture longitudinally through the first tissue to its distal cut end;

(8) repeating steps (1) through (7) for a second membrane;

(9) attaching the ends of the sutures to the second tissue.

* * * * *